United States Patent
Goedeke et al.

(10) Patent No.: US 7,319,962 B2
(45) Date of Patent: Jan. 15, 2008

(54) AUTOMATIC VOICE AND DATA RECOGNITION FOR IMPLANTED MEDICAL DEVICE INSTRUMENT SYSTEMS

(75) Inventors: Steven D. Goedeke, Forest Lake, MN (US); David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 814 days.

(21) Appl. No.: 09/731,178

(22) Filed: Dec. 6, 2000

(65) Prior Publication Data

US 2001/0032085 A1    Oct. 18, 2001

Related U.S. Application Data

(60) Provisional application No. 60/173,071, filed on Dec. 24, 1999.

(51) Int. Cl.
*G10L 21/00* (2006.01)
*A61N 1/08* (2006.01)

(52) U.S. Cl. .......................... 704/275; 607/30; 607/60

(58) Field of Classification Search ................ 704/270, 704/275, 523; 600/523; 607/30, 32, 60, 607/92
See application file for complete search history.

(56) References Cited

U.S. PATENT DOCUMENTS

| | | | |
|---|---|---|---|
| 4,737,976 A | | 4/1988 | Borth et al. |
| 4,974,191 A | * | 11/1990 | Amirghodsi et al. ............ 704/8 |
| 5,054,082 A | * | 10/1991 | Smith et al. .................. 704/275 |
| H1347 H | | 8/1994 | Greeninger et al. |
| 5,544,654 A | * | 8/1996 | Murphy et al. ............... 600/443 |
| 5,664,061 A | * | 9/1997 | Andreshak et al. .......... 704/275 |
| 5,752,976 A | * | 5/1998 | Duffin et al. ................. 607/32 |
| 5,761,641 A | * | 6/1998 | Rozak et al. ................. 704/275 |
| 5,774,841 A | * | 6/1998 | Salazar et al. ............... 704/225 |
| 5,792,204 A | | 8/1998 | Snell |
| 5,898,459 A | * | 4/1999 | Smith et al. ............. 348/219.1 |
| 5,940,118 A | * | 8/1999 | Van Schyndel .......... 348/14.05 |
| 5,970,457 A | * | 10/1999 | Brant et al. .................. 704/275 |

(Continued)

*Primary Examiner*—Michael Opsasnick
(74) *Attorney, Agent, or Firm*—Daniel G. Chapik

(57) ABSTRACT

The voice controlled system of the present invention permits hands-free interactive control of a medical data processing instrument that interfaces with an implanted medical device. In an example embodiment, the system includes a microphone and a speech recognition circuit coupled to the microphone and adapted to recognize an audio signal from the microphone. The audio signal corresponds to one of a subset of commands from a set of commands and each command corresponds to a task to be performed on the implanted medical device. The speech recognition circuit is further adapted to convert the audio signal into a selection code and match the selection code to one of the subset of commands. The system further includes a display device and a processor arrangement coupled to the speech recognition circuit and to the display device. The processor arrangement is configured to receive data indicative of an implanted medical device state and select the subset of commands as a function of the device state. The processor arrangement is also configured to display the device state data and the subset of commands and generate a control signal in response to the selection code match. The system also includes a medical data processing instrument coupled to the processor arrangement that is adapted to, in response to the control signal, execute the one of the subset of commands and to display data generated in response to execution of the one of the subset of commands.

30 Claims, 2 Drawing Sheets

U.S. PATENT DOCUMENTS

| | | | |
|---|---|---|---|
| 6,073,101 A * | 6/2000 | Maes | 704/275 |
| 6,101,338 A * | 8/2000 | Bernardi et al. | 396/287 |
| 6,115,628 A * | 9/2000 | Stadler et al. | 600/517 |
| 6,141,592 A * | 10/2000 | Pauly | 607/60 |
| 6,169,925 B1 * | 1/2001 | Villaseca et al. | 607/60 |
| 6,223,083 B1 * | 4/2001 | Rosar | 607/60 |
| 6,224,542 B1 * | 5/2001 | Chang et al. | 600/109 |
| 6,266,566 B1 * | 7/2001 | Nichols et al. | 607/30 |
| 6,278,975 B1 * | 8/2001 | Brant et al. | 704/275 |
| 6,292,698 B1 * | 9/2001 | Duffin et al. | 607/32 |
| 6,442,430 B1 * | 8/2002 | Ferek-Petric | 607/32 |
| 6,450,172 B1 * | 9/2002 | Hartlaub et al. | 128/899 |
| 6,564,104 B2 * | 5/2003 | Nelson et al. | 607/60 |
| 6,665,565 B1 * | 12/2003 | Stomberg et al. | 607/31 |

* cited by examiner

US 7,319,962 B2

AUTOMATIC VOICE AND DATA RECOGNITION FOR IMPLANTED MEDICAL DEVICE INSTRUMENT SYSTEMS

RELATED PATENT DOCUMENTS

This application claims priority to U.S. Provisional Application Ser. No. 60/173,071, filed on Dec. 24, 1999 (P-8896), entitled "Automatic Voice and Data Recognition for Medical Device Instrument Systems." The disclosure and drawings of the Provisional application are specifically incorporated herein by reference.

FIELD OF THE INVENTION

The present invention generally relates to the control of telemetry for implantable medical devices and instruments. Specifically, the invention relates to a method and a system for collecting diagnostic data from an implantable medical device (IMD).

BACKGROUND OF THE INVENTION

The present invention is compatible and complementary with the elements disclosed in the following pending applications: "Medical System Having Improved Telemetry," filed Jul. 19, 1999, Ser. No. 09/356,340, now U.S. Pat. No. 6,298,271; "System and Method for Transferring Information Relating to an Implantable Medical Device to a Remote Location," filed on Jul. 21, 1999, Ser. No. 09/358,081, now U.S. Pat. No. 6,250,309; "Apparatus and Method for Remote Troubleshooting, Maintenance and Upgrade of Implantable Device Systems," filed on Oct. 26, 1999, Ser. No. 09/426,741, now U.S. Pat. 6,442,433; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/429,960, now U.S. Pat. No. 6,363,282; "Apparatus and Method for Remote Self-Identification of Components in Medical Device Systems," filed Oct. 29,1999, Ser. No. 09/429,956; "Apparatus and Method to Automate Remote Software Updates of Medical Device Systems," filed Oct. 29, 1999, Ser. No. 09/429,960, now U.S. Pat. No. 6,363,282; "Method and Apparatus to Secure Data Transfer From Medical Device Systems," filed Nov. 2, 1999, Ser. No. 09/431,881 "Implantable Medical Device Programming Apparatus Having An Auxiliary Component Storage Compartment," filed Nov. 4, 1999, Ser. No. 09/433,477, now U.S. Pat. No. 6,411,851; "Remote Delivery Of Software-Based Training For Implantable Medical Device Systems," filed Nov. 10, 1999, Ser. No. 09/437,615, now U.S. Pat. No. 6,386,882; "Apparatus and Method for Remote Therapy and Diagnosis in Medical Devices Via Interface Systems," filed Dec. 14, 1999, Ser. No. 09/460,580, now U.S. Pat. No. 6,418,346; "Virtual Remote Monitor , Alert, Diagnostics and Programming For Implantable Medical Device Systems" filed Dec. 17, 1999, Ser. No. 09/466,284, now U.S. Pat. No. 6,497,655; "Instrumentation and Software for Remote Monitoring and Programming of Implantable Medical Devices (IMDs), filed Dec. 21, 1999, Ser. No. 60/172,937; "Application Proxy For Telecommunication-enabled Remote Medical Access Instruments," filed Dec. 23, 1999, Ser. No. 60/173,081; information Network Scheme For Interrogation Of Implantable Medical Devices (IMDs)," filed Dec. 24, 1999, Ser. No. 60/173,064, now U.S. Pat. No. 6,480,745; "Medical Device GUI For Cardiac Electrophysi-ology Display And Data Communications," filed Dec. 24, 1999, Ser. No. 60/173,065, now U.S. Pat. No. 6,473,638; "integrated Software System For Implantable Medical Device Installation And Management," filed Dec. 24, 1999, Ser. No. 60/173,082; "Dynamic Bandwidth Monitor And Adjuster For Remote Communications With A Medical Device," filed Dec. 24, 1999, Ser. No. 60/173,083, now U.S. Pat. No. 6,564,104 "Large-Scale Processing Loop For Implantable Medical Devices (IMDs)," filed Dec. 24, 1999, Ser. No. 60/173,079; "Chronic Real-Time Information Management Systems For Implantable Medical Devices (IMDs)," filed Dec. 24, 1999, Ser. No. 60/173,062; "Automatic Voice and Data Recognition For Medical Device Instrument Systems," filed Dec. 24, 1999, Ser. No. 60/173, 071 "Central Switchboard to Facilitate Remote Collaboration With Medical Instruments," filed Dec. 24, 1999, Ser. No. 60/173,080, now U.S. Pat. No. 6,442,432; which are all incorporated by reference herein in their entireties.

In recent years, implantable medical device technology has rapidly advanced. Sizes and weights of devices have decreased, while functionality has increased. These advances have created a corresponding demand for improved two-way communication or telemetry between the implantable medical device and an external device, for example, a programmer device. In a pacemaker system, for example, a programmer device downloads to an implanted pacemaker, data such as operating parameters. Likewise, data may flow from the implanted device to the programmer device. Modern pacemakers are capable of storing significant amounts of data about the patient, for example, the average heart rate, and information pertaining to the pacemaker itself, for example, battery voltage level. Generally, implanted device data is transmitted to the programmer device for review and evaluation by a physician.

Current programming devices typically include an extendible head portion that includes an antenna. The antenna is connected to other circuitry in the programmer device via a stretchable coil cable. Thus, the head portion can be positioned over the patient's implanted device site for programming or telemetry interrogation of the implanted device. Command instructions or data that are downloaded to the implanted device are referred to as downlink transmissions, and data transmitted from the implanted device to the programmer device are referred to as uplink transmissions.

Programming and pacing system analyzer units sometimes include graphic displays, keyboards or light pens for data entry and device control by a separate operator. During a surgical implant procedure the operator is sometimes located outside of the sterile environment of the operating room and receives commands for inputting data by the physician in the sterile environment. A programming head or wand is containing transceiver circuitry is positioned over a patient's implanted device site for programming and verification of proper placement of the implanted device during surgery. The implanting physician often cannot see the screen or display on the programmer because of the distance involved, size of screen and screen contrast limitations. This form of communication with the implanted device programming unit and operator is not only time consuming but the potential is high for miscommunication occurring between the physician and the programming unit operator.

SUMMARY OF THE INVENTION

Various embodiments of the present invention are directed to addressing the needs in connection with accurately inputting data and executing commands associated with medical data processing instruments using voice commands.

According to one embodiment of the invention, a system that interfaces with an implanted medical device uses a voice control system to control a medical data processing instrument that performs tasks on the implanted device. The system includes a microphone and a speech recognition circuit coupled to the microphone and adapted to recognize an audio signal from the microphone. The audio signal corresponds to one of a subset of commands from a set of commands and each command corresponds to a task to be performed on the implanted medical device. The speech recognition circuit is further adapted to convert the audio signal into a selection code and match the selection code to one of the subset of commands. The system further includes a display device and a processor arrangement coupled to the speech recognition circuit and to the display device. The processor arrangement is configured to receive data indicative of an implanted medical device state and select the subset of commands as a function of the device state. The processor arrangement is also configured to display the device state data and the subset of commands and generate a control signal in response to the selection code match. The system also includes a medical data processing instrument coupled to the processor arrangement that is adapted to, in response to the control signal, execute the one of the subset of commands and to display data generated in response to execution of the one of the subset of commands.

According to another embodiment of the invention, a method for interfacing with an implanted medical device uses voice control to control a medical data processing instrument that performs tasks on the implanted device. The method includes receiving data indicative of an implanted medical device state and selecting a subset of commands from a set of commands for performing tasks on the implanted medical device, the subset being selected as a function of the device state. The device state data along with the subset of commands is then displayed. An input audio signal from a microphone is then converted into a selection code, the input audio signal corresponding to one of the subset of commands. The selection code is then matched to one of the subset of commands and is then executed. Data generated by a medical data processing instrument is then received in response to execution of the one of the subset of commands.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
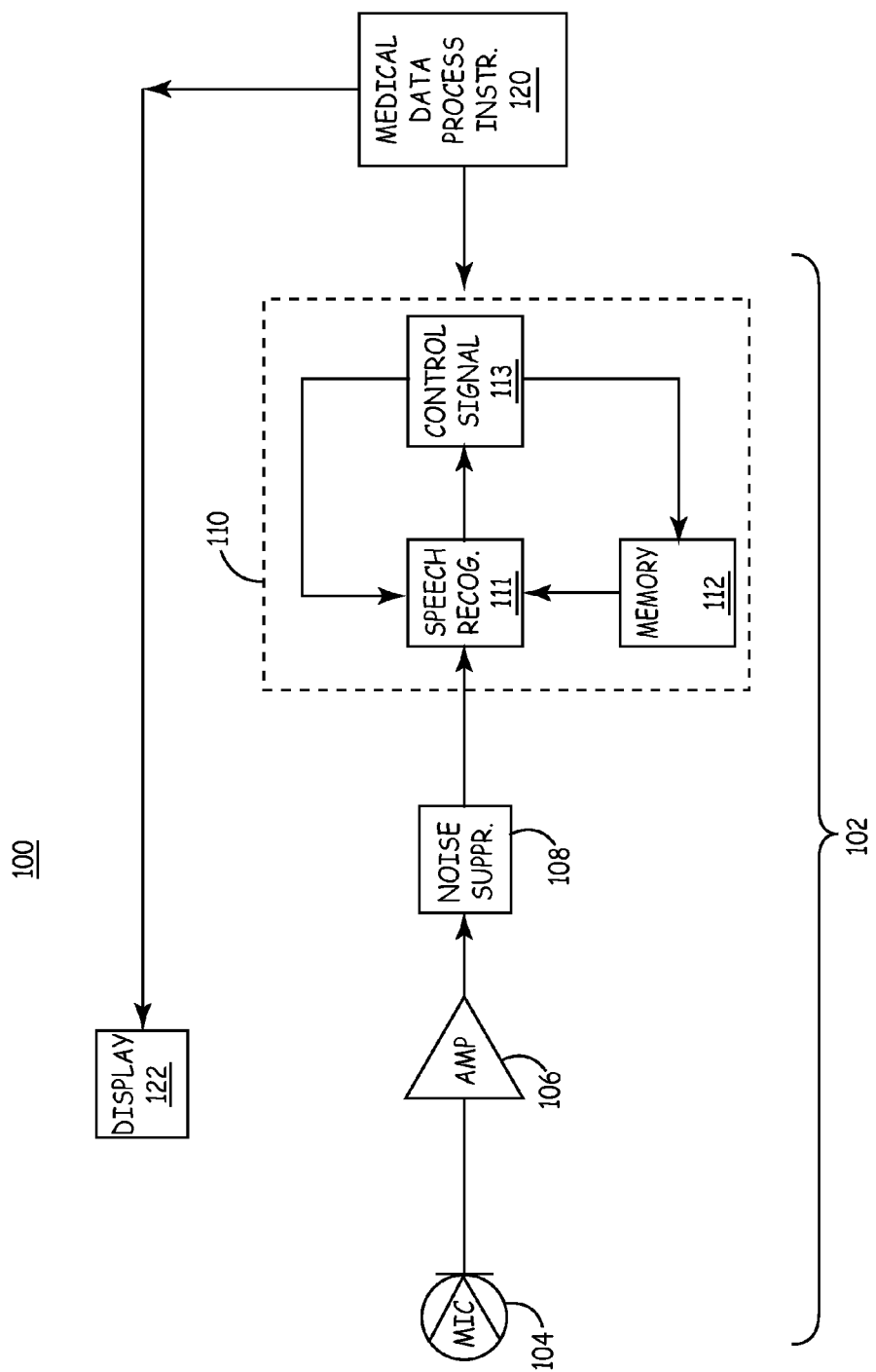
FIG. 1 illustrates a block diagram of an implanted medical device data processing instrument control system in accordance with an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to an automatic voice authentication and limited data set recognition system that is content limited, is reliable and allows for hands-free user interactive control of medical data processing instruments, such as pacing system analyzers and implanted device programming units. While the present invention is not necessarily limited to such an application, the invention will be better appreciated using a discussion of example embodiments in such a specific context.

In an example embodiment, a medical data processing instrument, which interfaces with an implanted medical device, is controllable via voice commands that are noise suppressed with a noise suppression circuit. The voice commands are selected as a function of the implanted device state and a subset of the commands are selected from a set of commands that are provided on a display. In this manner, the data processing instrument user selects a command from the subset of commands in the context of the implanted device state and the subset of commands displayed. Upon receipt of the voice command via a microphone coupled to a speech recognition control circuit, the noise suppression circuit generates a noise-suppressed speech signal in response to noise suppression information received from the microphone.

Referring now to the figures, FIG. 1 illustrates a voice controlled medical data processing instrument system 100 in accordance with an example embodiment of the present invention. System 100 includes a context speech recognition control system 102 coupled to a medical data processing instrument 120, including a context data display arrangement 122, that is adapted to interface with an implanted medical device. The context speech recognition control system includes a microphone 104 coupled to a bandpass amplifier 106, which is coupled to a dynamic noise suppression circuit 108 and which is in turn coupled to a context speech recognition control circuit 110. Speech recognition control circuit 110 includes a speech authentication circuit 111 having a digital signal processor arrangement, a template memory 112 and a control signal generator 113 coupled to circuit 111 and memory 112.

In an example embodiment, microphone 104 is a unidirectional microphone using a beam steering array arrangement to enhance voice sensitivity. Microphone 104 may be mounted on medical instrument 120 or alternatively, donned on the physician's clothing. In an example embodiment, the microphone is worn as a headset microphone or as a steerable microphone to improve voice command clarity. Bandpass amplifier 106 is used to reject background noise that is sensed by microphone 104. Noise suppression circuit 108 provides further filtering of background noise to improve the clarity of the voice command that is input to medical instrument 120. In particular, noise suppression circuit 108 generates a noise-suppressed speech signal in response to noise suppression information received from the microphone. For a detailed discussion on noise suppression circuits compatible with the present invention, reference is made to U.S. Pat. No. 4,737,976 to Borth et al., which is incorporated herein by reference.

Context data display 122 and the processor arrangement of the speech authentication circuit 111 are configured to display data indicating a recent implanted medical device state along with a corresponding set of command options. Each of the commands of the command options are executable for further processing of the recent implanted medical device state by the medical data processing instrument 120. In one example application, instrument 120 is a programmer-analyzer that is used during implant medical device surgery to perform any one of the following: to test the position of the leads within a patient's heart, to set the threshold electrical energy delivered to the patient's heart by the implanted device, or to monitor the electrical signals produced by the patient's heart. Any or all of these actions are performed on demand and serve to further process the implanted device from its current or recent state into a new state when a certain command is received by instrument 120. For a detailed discussion of the actions that are performed by a programmer-analyzer, reference is made to U.S. Pat. No. 5,792,204 to Snell, which is incorporated herein by reference.

Once the command is executed by medical instrument 120, the implanted device state data and available subset of commands corresponding to a particular implanted device state are provided via the display. In various embodiments, the display includes a display screen, a printed report generated by a printer, and/or an audio arrangement that emits an audible signal indicating the implanted device state and command options. For a detailed discussion of the operation of a programmer-analyzer, reference is made to U.S. Statutory Invention Registration H1347 to Greeninger et al, which is assigned to the Assignee of the present invention and which is incorporated herein by reference.

The speech recognition control system of the present invention overcomes the drawbacks of current medical instruments, such as light pen data entry systems, which have exhibited a higher failure rate than is desirable, and voice data entry systems (e.g., Dragon Systems—Naturally Speaking Professional) that are slow, are prone to error and are incapable of deciphering between the various voices that are sensed by the microphone. The speech recognition control system of the present invention uses automatic voice authentication and limited data set recognition, which are context limited, for hands-free user interactive control of the medical instrument 120. With the speech recognition control system of the present invention, proper voice selection and distinction among several individuals in the operating room is possible such that only the physician and the programmer operator control the functions of the medical data processing instrument 120. Speech recognition is also simplified and reliability is improved since system 102 need only select voice commands from a limited vocabulary list in memory arrangement 112.

In this example embodiment, speech authentication circuit 111 is adapted to recognize speech sets received from microphone 104 that include a command that is voice selected from the subset of commands that are displayed on the display 122. Speech authentication circuit 111 processes the command selected from the subset of commands through template memory 112 to ensure that the command is recognizable by the system. The control signal circuit 113 signals the medical data processing instrument 120 to respond to the speech sets received from the microphone. Medical instrument 120 is adapted to display data generated in response to execution of the voice select command from the subset of commands.

Figure 2:
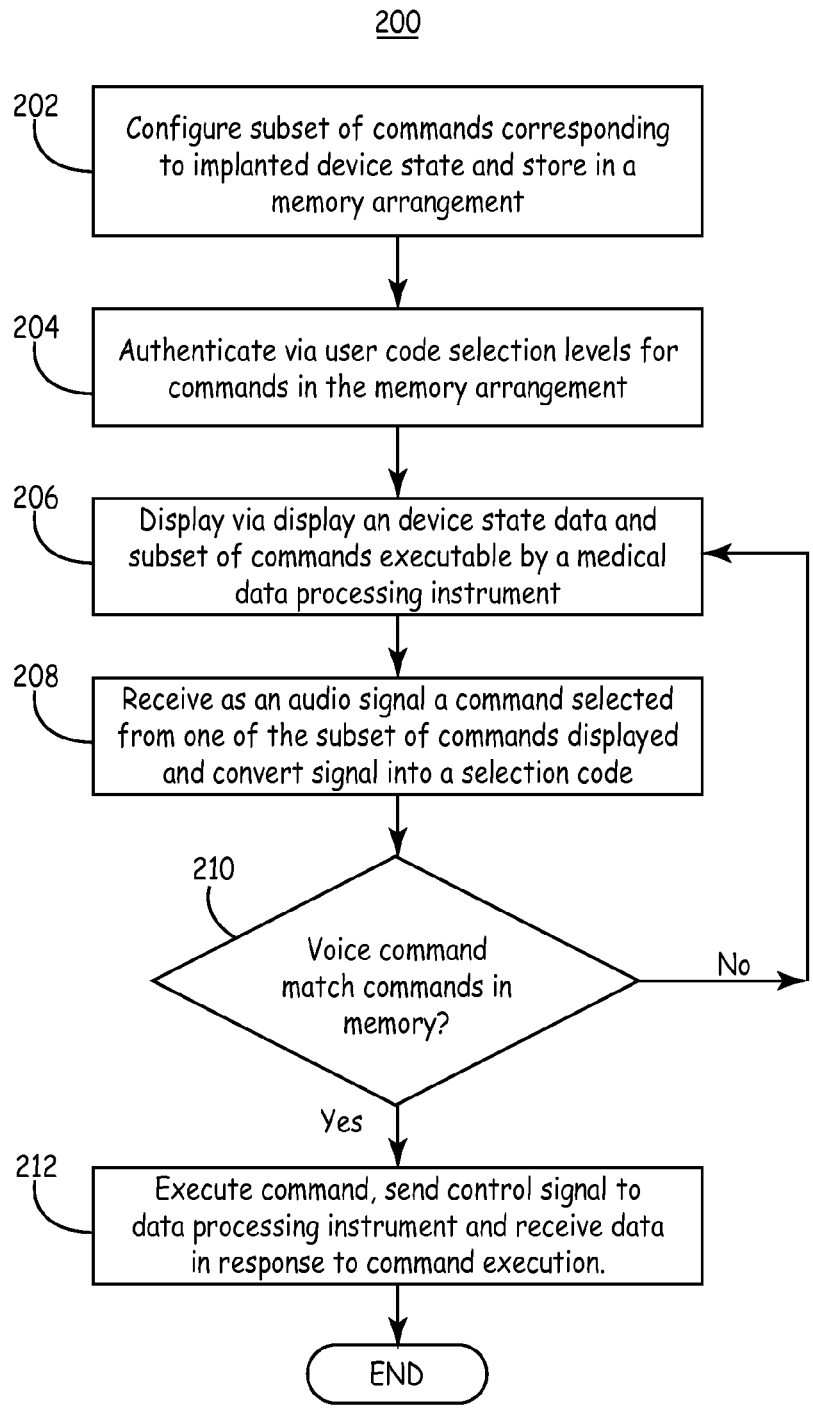
FIG. 2 is a flowchart illustrating the manner of inputting data and executing commands on a medical data processing instrument in accordance with an example embodiment of the invention.

Referring now to FIG. 2, a flowchart 200 illustrates the manner of programming and controlling a medical data processing system that interfaces with an implanted medical device in accordance with an example embodiment of the present invention. At step 202, a subset of commands (of a set of commands) corresponding to each implanted device state are generated, configured and stored in template memory 112 for later display. Template memory 112 has a limited set of recognizable words which, in this example embodiment, includes about 30-50 words based on the context of the screen display, the specific commands available in the context of this screen (e.g., hypertext) and/or the present state of the implanted device under control. This approach provides a more reliable and less compute intensive voice authentication and recognition system. The authentication and recognition algorithm is based upon phonic assembly of words normally used with implanted devices. In this example embodiment, the speech authentication circuit in combination with the memory arrangement involves operator training in developing the dictionary of words to be stored in the template memory but does not need operator involvement in developing word recognition. In another embodiment, operator training is not necessary since system 102 is configured to have a limited vocabulary in memory from which command selections are made.

At step 204, the speech authentication circuit is configured via a code to recognize certain users (physician, nurse, etc.) along with their corresponding authorized selection levels and in the manner that a user selects the commands. At step 206, display 122 displays data indicating the implanted device state along with the subset of corresponding commands. At step 208, a voice selection of one of the displayed subset of commands is made by the physician and received by the speech recognition control circuit. At step 210, the command is processed as an audio signal from the microphone and converted to a selection code. A determination is then made whether the voice command selection code matches or corresponds to the one of the subset of commands in memory for the displayed implanted device state.

If the command is proper (code matches) with respect to the displayed device state and subset of commands provided from memory 112, a control signal from control signal circuit 113 is transmitted to medical data processing instrument 120 to execute the command and perform the task. The control circuit 113 generates control signals based on received commands from the speech recognition circuit 111, thereafter providing an input control signal to the medical instrument. Additional implanted device data is then displayed in response to the medical data processing instrument executing the voice-selected command. In one example embodiment, the additional data displayed includes a subsequent device state along with another subset of commands. If the command is improper or not recognized by the speech control circuit 111 and memory 112, the display does not change and the flow of the process returns to step 206. In another example embodiment, a message is displayed on the display, or an audible tone is generated, indicating to the physician that the selected command was either executed (confirmation message or tone) or was not executed (error message or error tone). In yet another embodiment, the command confirmation, positive or negative, is represented by an audible voice repetition of the given command and confirmation of receipt/processing of the command.

In an example embodiment, a remote communications link is optionally established at step 204 as part of the authentication process with an additional data processing center that includes a physician or technicians that specialize in the area of implanted devices. The additional data processing center is remotely located and the retrieval of information is performed over a communications network. At the center, a physician or healthcare specialist provides remote analysis of the data and approves changes in therapy or diagnosis via voice commands that are sent to the speech recognition circuit 111.

The present invention provides, in an example application, non-invasive clinical data measurement or control of various IMDs, using the voice controlled medical instrument system, including but not limited to drug pumps, neurological implants, nerve stimulators, various cardiac implants and equivalent medical devices. The present invention is compatible to a number of techniques for programming and interrogating implanted medical devices. In addition, embodiments described are compatible with remote patient management systems that interact with remote data and expert data centers and compatible with a data communications system that enables the transfer of clinical data from the patient to a remote location for evaluation, analysis, data reposition, and clinical evaluation.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A system for interfacing with an implanted medical device, the system comprising:
   a microphone;
   a speech recognition circuit coupled to the microphone and adapted to recognize an audio signal from the microphone, the audio signal corresponding to one of a subset of commands from a set of commands and each command corresponding to a task to be performed on the implanted medical device, the speech recognition circuit further adapted to convert the audio signal into a selection code and match the selection code to one of the subset of commands;
   a display device;
   a processor arrangement coupled to the speech recognition circuit, to the display device, and in communication with the implanted medical device, the processor arrangement configured to receive data indicative of an implanted medical device state from the implanted medical device and automatically select the subset of commands as a function of the device state, the processor arrangement configured to display the device state data and the subset of commands, and generate a control signal in response to the selection code match; and
   a medical data processing instrument coupled to the processor arrangement and adapted to, in response to the control signal, execute the one of the subset of commands and to display data generated in response to execution of the one of the subset of commands.

2. The system of claim 1, further including a bandpass amplifier circuit coupled to the microphone and adapted to reject ambient background noise signals that are not speech generated.

3. The system of claim 1, further including a noise suppression circuit coupled to the microphone and adapted to produce a noise-suppressed speech signal in response to noise suppression information received from the microphone.

4. The system of claim 1, wherein the medical data processing instrument includes a pacing system analyzer.

5. The system of claim 1, wherein the medical data processing instrument includes an implanted medical device programming unit adapted to interrogate and program the implanted device.

6. The system of claim 1, wherein the microphone is a unidirectional microphone arrangement adapted to be donned and steered by a user of the medical data processing instrument, thereby reducing background noise.

7. The system of claim 1, further comprising an audio circuit coupled to the speech recognition circuit configured and arranged to reproduce and repeat a voice selected command and to produce an audio signal confirming execution of the voice selected command.

8. The system of claim 1, wherein the speech recognition circuit is coupled to the medical data processing instrument via a communications network.

9. The system of claim 1, further comprising an audio circuit coupled to the speech recognition circuit configured and arranged to produce an audio signal confirming receipt of a voice selected command from the subset of commands.

10. The system of claim 9, wherein the audio circuit is configured and arranged to produce an audio signal representing the device state with the subset of commands.

11. The system of claim 1, wherein the display includes a display screen adapted for use by a user of the medical data processing instrument and coupled to the speech recognition circuit and the processor arrangement.

12. The system of claim 11, wherein the microphone is a unidirectional microphone mounted on the display screen and coupled to the medical data processing instrument, thereby reducing background noise.

13. The system of claim 12, wherein the microphone is adapted to be directionally steered by a user of the medical data processing instrument for improved audio signal clarity.

14. The system of claim 1, wherein the speech recognition circuit further includes a memory arrangement configured to store the set of commands and the device state data and adapted to be accessed by the processor upon recognition of the audio signal received from the microphone.

15. The system of claim 14, wherein the memory arrangement is adapted to store the subset of commands corresponding to at least one of a plurality of implanted device states.

16. The system of claim 14, wherein the speech recognition circuit further includes a control signal circuit adapted to generate control signals for the medical data processing instrument in response to the selection code match.

17. The system of claim 14, wherein the speech recognition circuit and the processor are adapted to interact with a user to generate the set of commands to be stored in the memory arrangement.

18. The system of claim 17, wherein the processor is adapted to receive and validate the user via a user selection code, the user selection code providing access to differing levels of commands for controlling the data processing instrument.

19. A system for interfacing with an implanted medical device, the method comprising:
   means for receiving data indicative of an implanted medical device state from the implanted medical device;
   means for selecting a subset of commands from a set of commands for performing tasks on the implanted medical device, the subset being selected by the system as a function of the device state communicated from the implanted medical device;

means for displaying the device state data along with the subset of commands;

means for converting an input audio signal from a microphone into a selection code, the input audio signal corresponding to one of the subset of commands;

means for matching the selection code to one of the subset of commands;

means for executing the one of the subset of commands; and means for receiving data generated by a medical data processing instrument in response to execution of the one of the subset of commands.

20. A method for interfacing with an implanted medical device, the method comprising:

receiving data indicative of an implanted medical device state from the implanted medical device;

selecting a subset of commands from a set of commands for performing tasks on the implanted medical device, the subset being automatically selected by a processor based on the received device state data;

displaying the device state data along with the subset of commands;

converting an input audio signal from a microphone into a selection code, the input audio signal corresponding to one of the subset of commands;

matching the selection code to one of the subset of commands;

executing The one of the subset of commands; and receiving data generated by a medical data processing instrument in response to execution of the one of the subset of commands.

21. The method of claim 20, wherein the step of executing the one of the subset of commands includes the step of validating speech sets received via a memory arrangement coupled to the processor, the memory arrangement having the set of commands stored therein.

22. The method of claim 20, further comprising the step of producing an audio signal representing the device state with the subset of commands before the step of executing the one of the subset of commands.

23. The method of claim 20, further comprising the step of suppressing noise from the input audio signal before converting the audio signal into a selection code.

24. The method of claim 20, further comprising the steps of:

configuring the set of commands via a plurality of voice commands provided by a user of the medical data processing instrument before the step of receiving data indicative of the device state; and storing the set of commands in a memory arrangement for display.

25. The method of claim 24, further comprising the step of receiving and validating a user via a user selection code, the user selection code providing access to differing levels of commands for controlling the processing instrument before the step of receiving the voice selected command.

26. A method for controlling a medical data processing instrument that interfaces with an implanted medical device, the method comprising:

receiving data from the Implanted medical device indicative of the a device state;

utilizing a processor to automatically select a subset of commands from a set of commands based on the received data;

displaying the implanted device state data along with the subset of commands;

receiving a voice command selected from one of the subset of commands;

processing the selected command via a processor and a memory arrangement, the memory arrangement including the set of commands along with a set of control signals, the control signals used for controlling the data processing instrument;

transmitting to the data processing instrument the control signal for executing the selected command for performing a task on the implanted device; and displaying device state data generated by the data processing instrument in response to executing the selected command.

27. The method of claim 26, further comprising the step of producing a noise-suppressed speech signal corresponding to noise suppression information received after the voice command is received.

28. The method of claim 26, further comprising the step of generating the set of commands to be stored in the memory arrangement via voice commands provided by a user of the data processing arrangement before the step of displaying the device state data.

29. The method of claim 28, further comprising the step of receiving and authenticating a user selection code for providing access to differing levels of command options before the step of receiving the voice command.

30. A system for controlling a medical data processing instrument that interfaces with an implanted medical device, the system comprising:

means for receiving device state data from the implanted medical device and automatically selecting a subset of commands from a set of commands based upon the device state data;

means for displaying the implanted device state data along with the subset of commands;

means for receiving a voice command selected from one of the subset of commands;

means for processing the selected command via a processor and a memory arrangement, the memory arrangement including the set of commands along with a set of control signals, the control signals used for controlling the data processing instrument;

means for transmitting to the data processing instrument the control signal for executing the selected command for performing a task on the implanted device; and means for displaying device state data generated by the data processing instrument in response to executing the selected command.

* * * * *